United States Patent
Weller et al.

[11] Patent Number: 6,159,924
[45] Date of Patent: Dec. 12, 2000

[54] LOW RESIDUE AQUEOUS HARD SURFACE CLEANING AND DISINFECTING COMPOSITIONS

[75] Inventors: Jeanne Marie Weller, Glen Rock, N.J.; Kenneth A. Harrison, Goshen, N.Y.; Ann Marie Lynch, Glen Rock, N.J.

[73] Assignee: Reckitt Benckiser Inc., Wayne, N.J.

[21] Appl. No.: 09/351,204

[22] Filed: Jul. 9, 1999

Related U.S. Application Data

[60] Provisional application No. 60/094,054, Jul. 24, 1998.

[51] Int. Cl.$^7$ ................ C11D 1/62; C11D 3/44; C11D 1/75; C11D 3/22
[52] U.S. Cl. ............ 510/384; 510/182; 510/199; 510/237; 510/238; 510/245; 510/362; 510/365; 510/382; 510/384; 510/391; 510/432; 510/470; 510/503; 510/504
[58] Field of Search .................. 510/182, 199, 510/237, 238, 245, 362, 365, 382, 384, 391, 432, 470, 503, 504

[56] References Cited

U.S. PATENT DOCUMENTS

| | | | |
|---|---|---|---|
| 3,994,744 | 11/1976 | Anderle et al. | 134/4 |
| 4,002,571 | 1/1977 | Anderle et al. | 252/90 |
| 4,606,850 | 8/1986 | Malik | 252/528 |
| 4,859,359 | 8/1989 | DeMatteo et al. | 252/174.15 |
| 4,880,558 | 11/1989 | Jost et al. | 252/174.23 |
| 5,330,674 | 7/1994 | Urfer et al. | 252/176.17 |
| 5,454,984 | 10/1995 | Graubart et al. | 252/547 |
| 5,716,921 | 2/1998 | Neumiller | 510/181 |
| 5,750,482 | 5/1998 | Cummings | 510/182 |
| 5,770,548 | 6/1998 | Leskowicz et al. | 510/181 |
| 5,798,324 | 8/1998 | Svoboda | 510/182 |
| 5,820,695 | 10/1998 | Lance-Gomez et al. | 134/42 |
| 5,849,681 | 12/1998 | Neumiller et al. | 510/182 |
| 5,869,601 | 2/1999 | Svoboda | 528/480 |
| 5,891,392 | 4/1999 | Monticello et al. | 422/28 |
| 5,895,781 | 4/1999 | Neumiller et al. | 510/238 |
| 5,910,475 | 6/1999 | Nuemiller et al. | 510/238 |
| 5,929,016 | 7/1999 | Harrison | 510/384 |
| 5,929,024 | 7/1999 | Stringer et al. | 510/504 |
| 5,948,742 | 9/1999 | Chang et al. | 510/191 |

FOREIGN PATENT DOCUMENTS 0 691 397 A2  10/1996  European Pat. Off. .......... C11D 3/00

OTHER PUBLICATIONS

PCT International Search Report for PCT/GB99/02212 dated Oct. 28, 1999.

*Primary Examiner*—Yogendra Gupta
*Assistant Examiner*—Charles Boyer
*Attorney, Agent, or Firm*—Fish & Richardson P.C.

[57] ABSTRACT

Aqueous based cleaning compositions simultaneously featuring disinfecting, low residue deposit and good cleaning characteristics are provided. The compositions include one or more quaternary amine compounds as disinfecting active agents, an organic solvent system, one or more amine oxides, one or more nonionic alkylpolyglycosides, water and optionally further conventional additives including pH buffers, dyes, fragrances and the like.

9 Claims, No Drawings

LOW RESIDUE AQUEOUS HARD SURFACE CLEANING AND DISINFECTING COMPOSITIONS

This application claims benefit of Provisional Application 60/094,054 filed Jul. 24, 1998.

Cleaning compositions are commercially important products and enjoy a wide field of utility in assisting in the removal of dirt and grime from surfaces, especially those characterized as useful with "hard surfaces". While the art is replete with various formulations which provide some cleaning benefit and perhaps some disinfecting benefit to surfaces, few such formulations are sufficiently formulated so to be effective sanitizing and cleaning compositions and to appropriately satisfy the registration requirements of the United States Environmental Protection Administration ("EPA") as a "hospital strength" disinfectant. At the same time, it is not believed that there are known to the art such compositions which in addition to disinfection, which deposit minimal residues, and which also dry to an essentially streak free finish.

Thus, it is understood that there is a present and continuing need for cleaning products which simultaneously disinfect, leave a minimum of discernible residue, clean well, and are inexpensive. This need is further heightened when considered conjointly with the need for compositions which meet current requirements of the United States' Environmental Protection Administration, especially as hospital strength disinfecting compositions.

One object of the invention is to provide an aqueous liquid disinfectant cleaner which is particularly useful for cleaning and disinfecting hard surfaces particularly where effective cleaning, low streaking and low visible residue characteristics are desired. These compositions are especially useful in cleaning and disinfecting of hard surfaces, particularly polished or enameled metal surfaces, as well as on glass surfaces.

It is still further object of the invention to provide an aqueous cleaning and disinfecting composition which may be categorized as a hospital strength disinfecting composition in accordance with current United States Environmental Protection Administration requirements.

These and other objects of the invention shall be more apparent from a reading of the specification and of the claims attached.

According to one aspect of the present invention there is provided an aqueous cleaning composition which provides disinfecting and cleaning characteristics to hard surfaces, which comprises (or preferably consists essentially of) the following constituents:

A) one or more quaternary ammonium surfactant compounds having germicidal properties;

B) a solvent system which consists of two or more different glycol ethers in conjunction with a low molecular weight monohydric alcohol wherein the monohydric alcohol comprises less than one-half, preferably less than one-fourth of the total of the weights of the two or more glycol ethers;

C) one or more amine oxide compounds;

D) one or more nonionic alkylpolyglycoside compounds;

E) water.

The compositions may include one or more further optional additive constituents, sometimes referred to as adjuvants, in minor, but effective amounts. The compositions are characterized in providing a disinfecting effect, and particularly preferred embodiments are sufficient to be rated a "broad spectrum disinfectant" yet more desirably are sufficient to be rated a "hospital strength disinfectant" according to EPA guidelines. Further, particularly preferred embodiments are essentially non-streaking.

According to certain particularly preferred embodiment the compositions are essentially free of alkanolamines, particularly mono-, di- and tri- alkanolamines which include for example; ethanolamine, diethanolamine, triethanolamine and isopropanolamine.

According to a further aspect of the invention there is provided a process for the cleaning and disinfecting of a hard surface in need of such treatment which comprises the step of: applying an effective amount of the composition described herein to the hard surface in need of such treatment. Desirably, the composition is used to wet the hard surface in need of such treatment for a sufficient time period necessary to disinfect the surface, after which the treated hard surface may be wiped until substantially dry. Any remaining composition may be thereafter allowed to dry.

A) The compositions according to the invention include one or more quaternary ammonium surfactant compounds having germicidal properties. Exemplary useful quaternary ammonium compounds include quaternary ammonium germicides which may be characterized by the general structural formula:

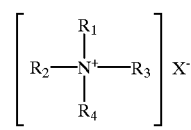

where at least one of $R_1$, $R_2$, $R_3$ and $R_4$ is a alkyl, aryl or alkylaryl substituent of from 6 to 26 carbon atoms, and desirably the entire cation portion of the molecule has a molecular weight of at least 165. The alkyl substituents may be long-chain alkyl, long-chain alkoxyaryl, long-chain alkylaryl, halogen-substituted long-chain alkylaryl, long-chain alkylphenoxyalkyl, arylalkyl, etc. The remaining substituents on the nitrogen atoms other than the abovementioned alkyl substituents are hydrocarbons usually containing no more than 12 carbon atoms. The substituents $R_1$, $R_2$, $R_3$ and $R_4$ may be straight-chained or may be branched, but are preferably straight-chained, and may include one or more amide, ether or ester linkages. The counterion X may be any salt-forming anion which permits water solubility of the quaternary ammonium complex. Exemplary counterions include halides, for example chloride, bromide or iodide, or methosulfate.

Preferred quaternary ammonium compounds which act as germicides and which are be found useful in the practice of the present invention include those which have the structural formula:

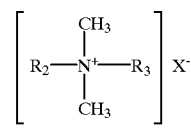

wherein $R_2$ and $R_3$ are the same or different $C_8$–$C_{12}$alkyl, or $R_2$ is $C_{12-16}$alkyl, $C_{8-18}$alkylethoxy, $C_{8-18}$alkylphenolethoxy and $R_3$ is benzyl, and X is a halide, for example chloride, bromide or iodide, saccharinate or methosulfate. The alkyl groups recited in $R_2$ and $R_3$ may be straight-chained or branched, but are preferably substantially linear.

Particularly useful quaternary germicides include compositions which include a single quaternary compound, as well as mixtures of two or more different quaternary compounds. Particularly useful quaternary germicides include those which are presently commercially available under the tradenames BARDAC, BARQUAT, BTC, LONZABAC and HYAMINE, available from Stepan Co. (Chicago Ill.) or Lonza Inc. (Basle, CH). Especially preferred compounds are described in the Examples.

It is to be understood that the quaternary ammonium compound constituent may be a single such compound, or may be a mixture of such compounds.

In the compositions according to the invention, the quaternary ammonium compound constituent is required to be present in amounts which are effective in exhibiting satisfactory germicidal activity against selected bacteria sought to be treated by the cleaning compositions. The quaternary ammonium compound need only be present in germicidally effective amounts. Generally, effective "hospital strength" germicidal efficacy meeting current EPA guidelines is provided when the quaternary ammonium compounds are present in an amount of from about 0.01% wt. to about 3 % wt. Desirably the quaternary ammonium compounds is present in an amount of from 0.01% wt. to about 0.5% wt, and yet more desirably from 0.01% wt. to 0.2 % wt. based on the total weight of the inventive compositions being taught herein.

B) The inventive compositions include a solvent system which consists of at least two different glycol ethers in conjunction with a low molecular weight monohydric alcohol wherein the monohydric alcohol comprises less than one-half of the total of the weights of the at least two glycol ethers. In preferred embodiment, the monohydric alcohol comprises not more than one-fourth of the total of the weights of the two or more glycol ethers. As the glycol ether constituent there may be used those having the general structure $R_a$—O—$R_b$—OH, wherein $R_a$ is an alkyl of 1 to 20 carbon atoms, or an aryl of at least 6 carbon atoms, and $R_b$ is an alkylene of 1 to 8 carbons or is an ether or polyether containing from 2 to 20 carbon atoms. Exemplary glycol ethers include propylene glycol methyl ether, dipropylene glycol methyl ether, tripropylene glycol methyl ether, propylene glycol isobutyl ether, ethylene glycol methyl ether, ethylene glycol ethyl ether, ethylene glycol butyl ether, diethylene glycol phenyl ether, propylene glycol phenol ether, dipropylene glycol monobutyl ether and mixtures thereof.

Preferably however, one glycol ether is propylene glycol n-butyl ether which has been observed to exhibit good cleaning; as the second and any further glycol ethers may be use any of those described above. In a particularly preferred embodiment, the sole glycol ethers in the composition are propylene glycol n-butyl ether and propylene glycol methyl ether. The solvent system also includes at least one low molecular weight monohydric alcohol, preferably the $C_1$–$C_5$ primary, secondary or tertiary alcohols. One particularly preferred monohydric alcohol is isopropanol. It is to be understood that mixtures of two or more alcohols may be used, but desirably only a single alcohol is used in the solvent system.

The solvent system, in total, comprises from 0.01–10% wt. of the inventive compositions, but preferably comprise 0.1–6% wt. Further the total amount of the monohydric alcohol in the solvent system comprises up to half of the total of the weights of the glycol ethers in the solvent systems. Preferably the ratio of the monohydric alcohol to the total weight of the glycol ethers is from 0.05–0.35:1, preferably 0.05–0.25:1 in respective parts by weight.

According to certain particularly preferred embodiments, the organic solvent system (B) consists solely of propylene glycol n-butyl ether and propylene glycol methyl ether, and isopropanol.

C) The present inventive compositions include one or more surfactant compounds based on amine oxide compounds. Such nonionic surfactants are known to the art and are available in commercial preparations, typically as a quantity of the surfactant compound dispersed in an aqueous carrier.

Such amine oxide compounds are particularly selected from other known surfactant compounds as they have been observed to provide not only requisite surface active characteristics and, compatibility with the quaternary ammonium cationic compounds but also have been observed by the inventor to assist in maintaining the phase stability of the inventive compositions over extended intervals of time and/or at high temperatures, up to about 120° F. Generally the compositions do not undergo phase separation at these temperatures. Such beneficial characteristics have been observed especially where the organic solvent is selected to be among the preferred, in particular to be the most preferred organic solvent system described above. Further, the present inventor has observed that these amine oxide compounds do not tend to contribute to a mottled or streaky appearance to the treated surface during drying. Additionally, these amine oxide compounds provide a cleaning benefit to the compositions.

Amine oxide compounds which are usefull in the compositions of the invention are known to the art. One general class of useful amine oxides include alkyl di(lower alkyl) amine oxides in which the alkyl group has about 10–20, and preferably 12–16 carbon atoms, and can be straight or branched chain, saturated or unsaturated. The lower alkyl groups include between 1 and 7 carbon atoms. Examples include lauryl dimethyl amine oxide, myristyl dimethyl amine oxide, dimethyl cocoamine oxide, dimethyl (hydrogenated tallow) amine oxide, and myristyl/palmityl dimethyl amine oxide. Further amine oxides include alkyl di(hydroxy lower alkyl) amine oxides in which the alkyl group has about 10–20, and preferably 12–16 carbon atoms, and can be straight or branched chain, saturated or unsaturated. Examples are bis(2-hydroxyethyl) cocoamine oxide, bis(2-hydroxyethyl) tallow amine oxide, and bis(2-hydroxyethyl) stearylamine oxide. Yet further useful amine oxides include alkylamidopropyl di(lower alkyl) amine oxides in which the alkyl group has about 10–20, and preferably 12–16 carbon atoms, and can be straight or branched chain, saturated or unsaturated. Examples are cocoamidopropyl dimethyl amine oxide and tallowamidopropyl dimethyl amine oxide.

Suitable amine oxides, including many of those recited above, include those which are presently commercially available and include those under the trade name Ammonyx® (Stepan Co., Chicago Ill.), as well as Barlox® (Lonza Inc., Fairlawn N.J.) With respect to the amine oxides, preferred are the alkyl di (lower alkyl) amine oxides in which the alkyl group has about 12–16 carbon atoms, of which most preferably lauryl amine oxides.

The amine oxide constituent forms from 0.01–2% wt. of the inventive compositions, preferably comprise from 0.01–1 % wt.

D) The inventive compositions also contain at least one nonionic surfactant based on an alkylpolyglycoside compound. Exemplary suitable compounds include alkyl monoglycosides and polyglycosides are prepared generally by reacting a monosaccharide, or a compound hydrolyzable to a monosaccharide with an alcohol such as a fatty alcohol in an acid medium.

Exemplary alkyl glycoside surfactants suitable for use in the practice of this invention include those which may be represented by the formula:

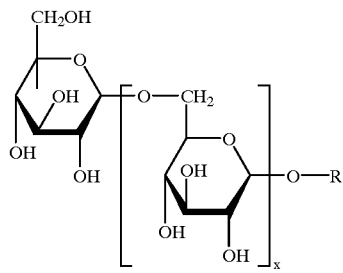

wherein:

R is an alkyl group, preferably a linear alkyl chain, which comprises $C_8$ to $C_{16}$ alkyl groups;

x is an integer value of from 0–3, inclusive.

Examples of such alkylpolyglycoside compounds according to this structure include: where R is comprised substantially of $C_8$ and $C_{10}$ alkyl chains yielding an average value of about 9.1 alkyl carbons per molecule (Glucopon® 220 UP, Glucopon® 225 DK); where R is comprised of $C_8$, $C_{10}$, $C_{12}$, $C_{14}$ and $C_{16}$ alkyl chains yielding an average value of about 10.3 alkyl carbons per molecule (Glucopon® 425); where R is comprised substantially of $C_{12}$, $C_{14}$ and $C_{16}$ alkyl chains yielding an average value of about 12.8 alkyl carbons per molecule (Glucopon® 600 UP, Glucopon® 625 CSUP, and Glucopon® 625 FE, all of which are available from Henkel Corp., Ambler Pa.). Also useful as the alkylpolyglycoside compound is Triton® CG-110 (Union Carbide Corp.).

A particularly preferred alkylglycoside is GLUCOPON 325N which is described as being a $C_9$–$C_{11}$ alkyl polyglycoside, also commonly referred to as D-glucopyranoside (from Henkel Corp, Ambler Pa.). Particularly preferred as the alkylpolyglycoside compounds are those illustrated in the Examples.

The nonionic alkylpolyglycoside compounds comprise from 0.01–5% wt., preferably considerably less, namely from 0.01–1.25% wt.

As is noted above, the compositions according to the invention are aqueous in nature. Water is added in order to provide to 100% by weight of the compositions of the invention. According to preferred embodiments, the inventive compositions are substantially aqueous and comprise at least 85% wt., more preferably at least 90% wt. of water. The water may be tap water, but is preferably distilled and is most preferably deionized water.

In particularly preferred embodiments, the inventive compositions are shelf stable aqueous cleaning and disinfecting composition which do not undesirably degrade when subjected to an elevated temperature over an extended period of time. More specifically, the inventive compositions do not suffer precipitation or phase separation when a sample composition is subjected to an accelerated aging testing at 120° F., for a four-week test period. As is known to the art, such a test is a harsh test, and a useful indicator of the long term shelf stability of the tested sample composition.

The compositions according to the invention may be categorized as "broad spectrum" disinfecting compositions as they exhibit antimicrobial efficacy against at least *Staphylococcus aureus,* and *Salmonella choleraesuis* in accordance with the AOAC Germicidal Spray Test known to those skilled in the art. In more preferred embodiments, the compositions according to the invention may be categorized as "hospital strength" type disinfecting compositions as they exhibit antimicrobial efficacy against all three of the bacteria: *Staphylococcus aureus, Salmonella choleraesuis,* and *Pseudomonas aeruginosa* in accordance with the AOAC Germicidal Spray Test. This test evaluates the antimicrobial efficacy of a composition against *Staphylococcus aureus* (gram positive type pathogenic bacteria) (ATCC 6538), *Salmonella choleraesuis* (gram negative type pathogenic bacteria) (ATCC 10708), and *Pseudomonas aeruginosa* (ATCC 15442). The testing is performed generally in accordance with the protocols outlined generally referred to as the AOAC Official Method 961.02 "Germicidal Spray Products as Disinfectants", as described in AOAC Official Methods of Analysis, 16th Ed., (1995) the contents of which are herein incorporated by reference. This test is herein interchangeably referred to as the AOAC Germicidal Spray Test.

In preferred and especially in most preferred embodiments of the invention the compositions may be characterized by being essentially non-streaking, and depositing very little residue. The compositions are especially useful in cleaning and disinfecting of hard surfaces, particularly polished or enameled metal surfaces which are frequently encountered on kitchen appliances, as well as on glass surfaces.

As noted, the compositions may include one or more optional additives which by way of non-limiting example include: coloring agents such as dyes and pigments, fragrances and fragrance solubilizers, pH adjusting agents, pH buffering agents, chelating agents, rheology modification agents, as well as one or more further nonionic surfactant compounds. Desirably, in order to reduce the likelihood of undesired buildup upon treated surfaces, especially hard surfaces, the total amounts of such optional additives is less than about 2% wt. but are desirably significantly less, such as less than about 0.5% wt. based on the total weight of the aqueous cleaning and disinfecting composition being provided herein. Optimally, the amounts of such further optional additives is kept to a minimum in order to minimize the amounts of non-volatile constituents in the compositions as a whole, which tend to contribute to an undesired streaky or mottled appearance of the composition during drying.

Useful as chelating agents include those known to the art, including by way of non-limiting example; aminopolycarboxylic acids and salts thereof wherein the amino nitrogen has attached thereto two or more substituent groups. Preferred chelating agents include acids and salts, especially the sodium and potassium salts of ethylenediaminetetraacetic acid, diethylenetriaminepentaacetic acid, N-hydroxyethylethylenediaminetriacetic acid, and of which the sodium salts of ethylenediaminetetraacetic acid may be particularly advantageously used.

The compositions according to the invention optionally but desirably include an amount of a pH adjusting agent or pH buffer composition. Such compositions include many which are known to the art and which are conventionally used. By way of non-limiting example pH adjusting agents include phosphorus containing compounds, monovalent and polyvalent salts such as of silicates, carbonates, hydroxides, aluminates, and borates, certain organic materials such as gluconates, succinates, maleates, and their alkali metal salts, mineral acids, organic acids, bases, tartrates and certain acetates. A particularly preferred material is sodium tetraborate decahydrate, commonly referred to as borax. Desirably the compositions according to the invention include an effective amount of an organic acid and/or an inorganic salt form thereof which may be used to adjust and maintain the pH of the compositions of the invention to the desired pH range. The inventive compositions are preferably alkaline in nature, desirably exhibit a pH 8–11, and more desirably a pH of about 9–11. Any such pH adjusting agent should be compatible with the other constituents present.

Further optional, but advantageously included constituents are one or more coloring agents; particularly useful are water soluble or water dispersible dyes. Further optional, but desirable constituent include fragrances, natural or synthetically produced. Such fragrances may be added in any conventional manner.

Each of the constituents described above, are per se, known to the art and are widely commercially available.

In accordance with a particularly preferred embodiment of the inventive composition, there is provided low residue ready to use aqueous hard surface cleaning and broad spectrum disinfecting composition comprising per 100% wt. (preferably, consisting essentially of):

A) 0.01–3% wt. of one or more quaternary ammonium surfactant compounds having germicidal properties;

B) 0.1–6% wt. of a solvent system which consists of two or more different glycol ethers in conjunction with a low molecular weight monohydric alcohol wherein the monohydric alcohol comprises less than one-half of the total of the weights of the two glycol ethers;

C) 0.01–2% wt. of one or more amine oxide compounds;

D) 0.01–5% wt. of one or more nonionic alkylpolyglycoside compounds;

E) at least 85% wt. water

0–0.5% wt. optional constituents;

wherein the compositions are characterized by leaving minimal residue, and forming a substantially uniform film during evaporative drying after being applied to a hard surface. The compositions of the invention can be prepared in a conventional manner such as by simply mixing the constituents in order to form the ultimate aqueous cleaning composition. The order of addition is not critical but beneficially the surfactant constituents are added to the water prior to any other constituents.

The compositions according to the invention are useful in the cleaning and/or disinfecting of surfaces, especially hard surfaces, having deposited soil thereon. In such a process, cleaning and disinfecting of such surfaces comprises the step of applying a soil releasing and disinfecting effective amount of a composition as taught herein to such a soiled surface. It is contemplated that where disinfection of the treated surface is a primary concern, that the composition is allowed to keep the treated hard surface wet for a sufficient period of time in order to achieve disinfection of the hard surface. Afterwards, the compositions are optionally but desirably wiped, scrubbed or otherwise physically contacted with the hard surface, and further optionally, may be subsequently rinsed from such a cleaned and disinfected hard surface. In certain applications, especially where undesirable soil deposits are heavy, the cleaning composition according to the invention may be left on the soiled area until it has effectively loosened the soil deposits after which it may then be wiped off, rinsed off, or otherwise removed. For particularly heavy deposits of such undesired soils, multiple applications may also be used. To ensure effective disinfection, a longer contact time, generally of 10 minutes is required.

The hard surface cleaner composition provided according to the invention can be desirably provided in an aerosolized form which is packaged in a pressurized container, or may be supplied in a ready-to-use form such as in a bottle or flask which further includes a manually operated spray dispensing container.

Whereas the present invention is intended to be produced and provided in the "ready-to-use" form described above, they may be diluted in a further amount of water to form a cleaning solution therefrom. Desirably however the compositions should be used "as is", that is to say without further dilution.

The following examples illustrate the superior properties of the formulations of the invention and particular preferred embodiments of the inventive compositions. The terms "parts by weight" or "percentage weight" are used interchangeably in the specification and in the following Examples wherein the weight percentages of each of the individual constituents are indicated in weight percent based on the total weight of the composition, unless indicated otherwise.

EXAMPLES

Exemplary formulations illustrating certain preferred embodiments of the inventive compositions and described in more detail in Table 1 below were formulated generally in accordance with the following protocol.

Into a suitably sized vessel, a measured amount of water was provided after which the constituents were added in the following sequence: surfactants, alcohol and glycol ethers, amine oxide, and lastly the coloring and fragrance constituents (if included). All of the constituents were supplied at room temperature, and mixing of the constituents was achieved by the use of a mechanical stirrer with a small diameter propeller at the end of its rotating shaft. Mixing, which generally lasted from 5 minutes to 120 minutes was maintained until the particular exemplary formulation appeared to be homogeneous. The exemplary compositions were readily pourable, and retained well mixed characteristics (i.e., stable mixtures) upon standing for extended periods.

The exact compositions of the example formulations are listed on Table 1, below wherein are indicated the weight percentages of the named constituents in their "as supplied" form, based on a composition total weight of 100% weight.

TABLE 1

|  | Ex. 1 | Ex. 2 | Ex. 3 | Ex. 4 | Ex. 5 | Ex. 6 | Ex. 7 |
| --- | --- | --- | --- | --- | --- | --- | --- |
| BTC 8358 | 0.027 | 0.027 | 0.027 | 0.027 | 0.027 | 0.027 | 0.027 |
| BTC 65NF | 0.172 | 0.172 | 0.172 | 0.172 | 0.172 | 0.172 | 0.172 |
| AMMONYX LO | 0.2 | 0.2 | 0.35 | 0.35 | 0.35 | 0.35 | 0.2 |
| DOWANOL PnB | 2.5 | 2.5 | 2.5 | 2.5 | 2.5 | 2.5 | 2.5 |
| DOWANOL PM | 2.5 | 2.5 | 2.5 | 2.5 | 2.5 | 2.5 | 2.5 |
| isopropanol | 0.4 | 0.4 | 0.4 | 0.4 | 0.4 | 0.4 | 0.4 |
| GLUCOPON 325N | 0.8 | 0.48 | 0.8 | 0.48 | 0.48 | 0.8 | 0.48 |
| borax | 0.05 | 0.05 | 0.05 | 0.05 | 0.05 | 0.05 | 0.05 |
| fragrance | 0.05 | 0.05 | 0.05 | 0.05 | 0.05 | 0.05 | 0.05 |
| dye | 0.11 | 0.11 | 0.11 | 0.11 | 0.11 | 0.11 | 0.11 |
| deionized water | to 100 | to 100 | to 100 | to 100 | to 100 | to 100 | to 100 |

The identity of the particular constituents recited in Table 1 are disclosed in particular detail in Table 2 below, wherein the weight percent of 'actives' in the particular constituent is also denoted.

TABLE 2

| | |
|---|---|
| BTC 8358 | alkyl dimethyl benzyl ammonium chloride (80% wt. actives) [Stepan Co.] |
| BTC 65NF | alkyl dimethyl benzyl ammonium chloride (50% wt. actives) [Stephan Co.] |
| AMMONYX LO | lauryl dimethyl amine oxide (30% wt. actives) [Stephan Co.] |
| DOWANOL PnB | propylene glycol n-butyl ether (100% wt. actives) [Dow Chem. Co.] |
| DOWANOL PM | propylene glycol methyl ether (100% wt. actives) [Dow Chem. Co.] |
| isopropanol | isopropanol |
| GLUCOPON 325N | $C_9$–$C_{11}$ alkyl polyglycoside (50% wt. actives) [Henkel Co., Ambler, PA] |
| borax | sodium tetraborate decahydrate (100% wt.) U.S. Borax Inc. |
| fragrance | proprietary composition |
| aqueous dye | proprietary composition |
| deionized water | deionized water |

The compositions of Table 1 were evaluated in accordance with one or more of the further tests elucidated below.

Evaluation of Antimicrobial Efficacy

A formulation according to Example 4 as described on Table 1 above was evaluated at different pH's in order to evaluate their antimicrobial efficacy against *Staphylococcus aureus* (gram positive type pathogenic bacteria) (ATCC 6538), *Salmonella choleraesuis* (gram negative type pathogenic bacteria) (ATCC 10708), and *Pseudomonas aeruginosa* (ATCC 15442). The testing was performed in accordance with the protocols outlined in AOAC Official Method 961.02 "Germicidal Spray Products as Disinfectants", as described in AOAC Official Methods of Analysis, 16$^{th}$ Ed., (1995).

As is appreciated by the skilled practitioner in the art, the results of the AOAC Germicidal Spray Test indicates the number of test substrates wherein the tested organism remains viable after contact for 10 minutes with a test disinfecting composition/total number of tested substrates (slides) evaluated in accordance with the AOAC Germicidal Spray Test. Thus, a result of "0/10" indicates that of 10 test substrates bearing the test organism and contacted for 10 minutes in a test disinfecting composition, 0 test substrates had viable (live) test organisms at the conclusion of the test. Such a result is excellent, illustrating the excellent disinfecting efficacy of the tested composition.

The results of this test is indicated on Table 3, following:

TABLE 3

| | Organisms Tested | | |
|---|---|---|---|
| | S. aureus | S. choleraesuis | P. aeruginosa |
| Ex. 4, pH = 10 | 0/10 | 0/10 | 0/10 |
| Ex. 4, pH = 10.5 | 0/10 | 0/10 | 0/10 |
| Ex. 4, pH = 10.82 | 0/10 | 0/10 | 0/10 |
| Ex. 4, pH = 11.28 | 0/10 | 0/10 | 0/10 |

As can be seen from the results, the compositions according to the invention exhibit excellent disinfecting properties.

Evaluation of Cleaning Efficacy

The compositions of the invention are expected to exhibit good cleaning efficacy.

Evaluation of Streaking Drying Characteristics

The compositions of the invention are expected to exhibit low streaking.

While described in terms of the presently preferred embodiments, it is to be understood that the present disclosure is to be interpreted as by way of illustration, and not by way of limitation, and that various modifications and alterations apparent to one skilled in the art may be made without departing from the scope and spirit of the present invention.

What is claimed is:

1. An aqueous cleaning composition which provides disinfecting and cleaning characteristics to hard surfaces, which comprises the following constituents:

A) from 0.01–3% one or more quaternary ammonium surfactant compounds having germicidal properties;

B) from 0.01–10% a solvent system which consists of two or more different glycol ethers in conjunction with a low molecular weight monohydric alcohol wherein the monohydric alcohol comprises less than one-half of the total of the weights of the two or more glycol ethers;

C) from 0.01–2% one or more amine oxide compounds;

D) from 0.01–5% one or more nonionic alkylpolyglycoside compounds;

E) water.

2. The composition according to claim 1 wherein the quaternary ammonium germicide is accordance with the following general structural formula:

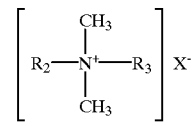

where:

$R_2$, $R_3$ may be $C_8$–$C_{12}$alkyl, or when $R_2$ is $C_{12-16}$alkyl, $C_{8-18}$alkylethoxy, $C_{8-18}$alkylphenolethoxy, $R_3$ is benzyl;

X is a halide.

3. An aqueous cleaning composition according to claim 1 which consists essentially of the following constituents:

A) 0.01–3% wt. of one or more quaternary ammonium surfactant compounds having germicidal properties;

B) 0.1–6% wt. of a solvent system which consists of two or more different glycol ethers in conjunction with a low molecular weight monohydric alcohol wherein the monohydric alcohol comprises less than one-half of the total of the weights of the two glycol ethers;

C) 0.01–2% wt. of one or more amine oxide compounds;

D) 0.01–5 % wt. of one or more nonionic alkylpolyglycoside compounds;

E) at least 85% wt. water

0–0.5% wt. optional constituents;

wherein the compositions are characterized by leaving minimal residue, and forming a substantially uniform film during evaporative drying after being applied to a hard surface.

4. A composition according to claim 1 wherein the compositions are characterized as being essentially free of alkanolamines.

5. A composition according to claim 1 wherein the alkylpolyglycoside compounds may be represented by the structure:

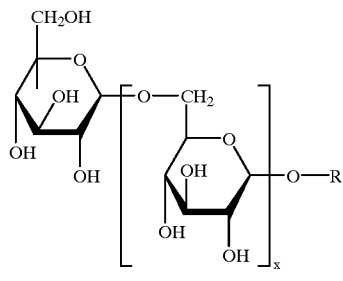

wherein:
R is an alkyl group, which comprises $C_8$ to $C_{16}$ alkyl groups;
x is an integer value of from 0–3, inclusive.

6. A process for the cleaning and disinfecting of a hard surface in need of such treatment which comprises the step of:
applying an effective amount of the composition according to claim 1 to a hard surface;
allowing the surface to remain wet for a time period necessary for disinfection; and,
optionally wiping the surface until substantially dry.

7. A composition according to claim 1 wherein the amine oxide compounds are selected from the group consisting of:
a) alkyl di(lower alkyl) amine oxides in which the alkyl group has about 10–20 carbon atoms;
b) alkyl di(hydroxy lower alkyl) amine oxides in which the alkyl group has about 10–20 carbon atoms; and,
c) alkylamidopropyl di(lower alkyl) amine oxides in which the alkyl group has about 10–20 carbon atoms.

8. An aqueous cleaning composition according to claim 1 characterized in being essentially free of alkanolamines.

9. An aqueous cleaning composition which provides disinfecting and cleaning characteristics to hard surfaces, which comprises the following constituents:

A) from 0.01–3% one or more quaternary ammonium surfactant compounds having germicidal properties wherein the quaternary ammonium germicide is accordance with the following general structural formula:

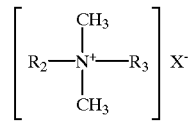

where:
$R_2$, $R_3$ may be $C_8$–$C_{12}$alkyl, or when $R_2$ is $C_{12-16}$alkyl, $C_{8-18}$alkylethoxy, $C_{8-18}$alkylphenolethoxy, $R_3$ is benzyl;
X is a halide;

B) from 0.01–10% a solvent system which consists of two or more different glycol ethers in conjunction with a low molecular weight monohydric alcohol wherein the monohydric alcohol comprises less than one-half of the total of the weights of the two or more glycol ethers;

C) from 0.01–2% one or more amine oxide compounds;

D) from 0.01–5% one or more nonionic alkylpolyglycoside compounds;

E) water, characterized in being essentially free of alkanolamines.

* * * * *